United States Patent [19]

Lee et al.

[11] Patent Number: 5,110,380
[45] Date of Patent: May 5, 1992

[54] DETONATING AN INSENSITIVE EXPLOSIVE

[75] Inventors: Kien-yin Lee, Los Alamos; Carlyle B. Storm, Santa Fe, both of N. Mex.

[73] Assignee: The United States of America as represented by the United States Department of Energy, Washington, D.C.

[21] Appl. No.: 767,603

[22] Filed: Sep. 30, 1991

[51] Int. Cl.$^5$ .............................................. C06G 25/34
[52] U.S. Cl. ........................................ 149/92; 149/88; 548/264.8
[58] Field of Search ................... 548/264.8; 149/92, 88

[56] References Cited

U.S. PATENT DOCUMENTS

| | | | |
|---|---|---|---|
| 3,054,800 | 9/1962 | Burchfield et al. | 260/299 |
| 3,111,524 | 11/1963 | Wiley et al. | 260/308 |
| 4,236,014 | 11/1980 | Lee et al. | 548/267 |
| 4,958,027 | 9/1990 | Laval et al. | 149/92 |
| 5,034,072 | 7/1991 | Becuwe | 149/19.4 |

OTHER PUBLICATIONS

Kien-yin Lee et al., "Use of Solvent Extraction in the Production of the Ammonium Salt of 3,5-Dinitro-1,2-,4-triazole," Ind. Eng. Chem. Process Des. Dev., vol. 20, No. 2 (1981).
Kien-yin Lee et al., "Preparation and Properties of 3-Amino-5-Nitro-1,2,4-Triazole," Los Alamos National Laboratory LA-11907-MS, issued Oct. 1990.
M. S. Pevzner et al., "Nitration of 5-Amino-1,2,4-Triazole and 5-Acetamindo-1,2,4-Triazole with Acetyl Nitrate and Nitronium Salts," Khim. Getero. Soed. 8, 1132-1135 (1979).
Yang-i Lin et al., "Selective Reduction of Nitro-Heterocycles with Sodium Sulfide in Aqueous p-Dioxane," J. Heterocyclic Chem. 17, 1273-75 (1980).
Nagaraj R. Ayyangar et al., "Partial Reduction of Dinitroarenes to Nitroanilines with Hydrazine Hydrate," Bull. Chem. Soc. Jpn. 56, 3159-3164 (1983).
W. W. Hartman et al., "2-Amino-4-Nitrophenol," Org. Syntheses, vol. III, pp. 82-84 (1955).

Primary Examiner—Stephen J. Lechert, Jr.
Attorney, Agent, or Firm—Richard J. Cordovano; Paul D. Gaetjens; William R. Moser

[57] ABSTRACT

A method for making 3-amino-5-nitro-1,2,4-triazole using ammonium 3,5-dinitro-1,2,4-triazole and hydrazine hydrate as starting materials and a method for providing energy derived from 3-amino-5-nitro-1,2,4-triazole.

2 Claims, No Drawings

DETONATING AN INSENSITIVE EXPLOSIVE

This invention relates to the field of chemistry and, more particularly, to explosives. This invention is the result of a contract with the Department of Energy (Contract No. W-7405-ENG-36).

BACKGROUND OF THE INVENTION

It is desirable to use explosives in weapons and other applications which are less sensitive than the common explosives RDX, TNT, and HMX, since there have been catastrophic explosions of munitions which use these compounds. Triaminotrinitrobenzene (TATB) and 3-nitro-1,2,4-triazol-5-one (NTO) are recently developed insensitive explosives which do not provide sufficient performance for certain applications. In preliminary characterization and sensitivity testing, it has been found that 3-amino-5-nitro-1,2,4-triazole (ANTA) is a promising insensitive high explosive. The detonation velocity of ANTA, calculated at crystal density, is higher than that of TATB. ANTA will be useful for providing chemical energy by means of detonation of ANTA. It is thermally stable up to about 250° C. and does not explode upon impact. The prior art process of synthesizing ANTA involves the acetylation of amino-1,2,4-triazole with acetic anhydride followed by nitration with acetyl nitrate and acid hydrolysis of the nitration product with hydrochloric acid. The yield from this process is only 1 or 2% and the process may be dangerous. Also, this prior art process produces hazardous waste materials.

The present inventive process for synthesizing ANTA does not require the use of strong acids. It can be accomplished in hours, in contrast to the days required for the prior art process, and utilizes a commercially available compound, hydrazine hydrate, as a starting material. There is no volatile hydrazine present at the end of the reaction, since it is isolated as hydrazine hydrochloride. Large scale production of ANTA using this process is quite feasible.

In addition to use in munitions, the insensitivity of ANTA makes it a promising candidate for explosive forming and welding and for severing connections between two components, such as separating the stages of spacecraft.

SUMMARY OF THE INVENTION

This invention is a method for making 3-amino-5-nitro-1,2,4-triazole using ammonium 3,5-dinitro-1,2,4-triazole and hydrazine hydrate as starting materials and a method of providing energy derived from 3-amino-5-nitro-1,2,4-triazole.

DETAILED DESCRIPTION OF THE INVENTION

ANTA is made by adding a quantity of the ammonium salt of 3,5-dinitro-1,2,4-triazole (ADNT) to a stirred container of hydrazine hydrate ($N_2H_4 \cdot H_2O$) at room temperature. After mixing the substances, the temperature of the reaction mixture is raised to a value in the range of from about 60° to about 80° C. The temperature is maintained within the range for a time period of from one to about three hours so that selective reduction of the ADNT by the hydrazine hydrate takes place. The product of the selective reduction is the hydrazinium salt of 3-amino-5-nitro-1,2,4-triazole (HANTA). After the reaction time period, the mixture is cooled to room temperature and a sufficient amount of hydrochloric acid (HCl) is added to bring the pH of the mixture to a value in a range of from about 2.0 to about 4.0. Upon addition of the HCl, ANTA precipitates out. The other product resulting from the addition of HCl to the reaction mixture comprising HANTA is hydrazine hydrochloride ($N_2H_4 \cdot HCl$).

ANTA has been synthesized by this process in batches of varying size. For example, 1.45 g (0.0082 moles) of ADNT was added to 0.0385 moles of hydrazine hydrate. The reaction mixture was stirred for 10 minutes, heated to 78°–80° C., and held at that temperature for 1.5 hours. The mixture was then cooled by adding water to it and then the pH of the mixture was brought to about 4.0 by adding 10 vol % HCl to the mixture. About 30 mL of 10 vol % HCl was required. The ANTA which precipitated out of the mixture was separated from the liquid and dried under vacuum. The amount of ANTA recovered was 0.99 g, which gives a yield of 94%. Yields of above 96% have been obtained in other experiments.

Use of a reaction temperature of about 80° C. is preferred in order that the required reaction period be relatively short. At higher temperatures, the desired product may not be obtained. The mixture may be cooled by allowing it to stand rather than by adding water to it. It is believed that the preferred pH upon addition of HCl to the mixture is 4.0. Recovery of ANTA from the solution may be done by filtration, centrifugation, or any other convenient means. It is preferable to use dilute HCl for reasons of safety, though concentrated HCl may also be used.

ADNT may be obtained by the method taught in U.S. Pat. No. 4,236,014 (Lee et al., issued Nov. 25, 1980), which is hereby incorporated into this patent application.

U.S. Pat. Nos. 3,054,800 and 3,111,524 may also be consulted in regard to the preparation of 3,5-dinitro-1,2,4-triazole.

In experimentation involving the inventive process, the progress of the reaction to form HANTA was monitored by silica gel thin layer chromatography (TLC). The solvent system used for spot development was a mixture consisting of five volumes of methylene chloride and one volume of ethanol with a few drops of acetic acid added. The TLC spots were observed under UV light. Carbon-13 and nitrogen-15 NMR analysis were used to verify that the precipitated product was ANTA and was free of impurities.

When the reaction product was isolated before the pH of the mixture was adjusted, the compound obtained was HANTA, which is not stable. When HANTA was heated to about 100° C. for a time period of about ten minutes or allowed to stand at room temperature for several days, the hydrazine component volatilized and ANTA resulted. It is believed that HANTA has never previously been synthesized.

ANTA is a lemon-colored crystalline compound, has little solubility in water, and is not hygroscopic. The result of small-scale screening tests of ANTA, together with its physical properties, are shown in the Table. Properties of TATB are shown for comparison.

TABLE

| | ANTA | TATB |
|---|---|---|
| Molecular Formula | $C_2H_3N_5O_2$ | $C_6H_6N_6O_6$ |
| Crystal Density (g/cm$^3$) | 1.82 | 1.94 |
| Melting Point (°C.) | 244 | 448–449 |

TABLE-continued

|                                      | ANTA          | TATB       |
|--------------------------------------|---------------|------------|
| Thermal Stability (°C.) DTA          | >240          | >350       |
| Vacuum Stability (mL/g/48 h/120° C.) | 0.3           | 0.2        |
| Impact Sensitivity. Type 12 (cm)     | >320          | >320       |
| Spark Sensitivity (J) (3-mil foil)   | >0.1          | 4.25       |
| Heat of Formation (kcal/mol)         | 21.0 ± 2.5    | −36.85     |
| D (km/s) (at crystal density)        | 8.46 (calc.)  | 7.98 (calc.) |
| Pcj (kbar) (at crystal density)      | 314 (calc.)   | 315 (calc.) |

What is claimed is:

1. A process for making 3-amino-5-nitro-1,2,4-triazole comprising:
   a. mixing ammonium 3,5-dinitro-1,2,4-trizaole and hydrazine hydrate;
   b. heating said mixture to a temperature in a range of from about 60° C. to about 80° C. and maintaining the temperature in said range for a time period of from about one hour to about three hours;
   c. cooling said mixture;
   d. adding a sufficient amount of hydrochloric acid to said mixture to bring the pH of said mixture to a value of from about 2.0 to about 4.0; and
   e. recovering 3-amino-5-nitro-1,2,4-triazole from said pH-adjusted mixture.

2. A method for providing chemical energy comprised of detonating a composition comprised of 3-amino-5-nitro-1,2,4-triazole.

* * * * *